United States Patent [19]

Shim

[11] 4,394,862
[45] Jul. 26, 1983

[54] METERING APPARATUS WITH DOWNLINE PRESSURE MONITORING SYSTEM

[75] Inventor: Norm Shim, Glenview, Ill.

[73] Assignee: Baxter Travenol Laboratories, Inc., Deerfield, Ill.

[21] Appl. No.: 180,939

[22] Filed: Aug. 25, 1980

[51] Int. Cl.³ ............................................. A61M 5/00
[52] U.S. Cl. ........................... 604/67; 128/DIG. 13; 417/38
[58] Field of Search .............. 128/214 E, 214 F, 214.2, 128/DIG. 12, DIG. 13; 417/38, 412, 476, 477

[56] References Cited

U.S. PATENT DOCUMENTS

| | | | |
|---|---|---|---|
| 2,927,582 | 3/1960 | Berkman et al. | 128/DIG. 3 |
| 3,091,239 | 5/1963 | Moeller | 128/214 F |
| 3,163,176 | 12/1964 | Darling | 128/214 E |
| 3,601,124 | 8/1971 | Petree | 128/214 E |
| 3,841,157 | 10/1974 | Willock | 73/389 |
| 3,901,231 | 8/1975 | Olson | 128/214 F |
| 4,210,138 | 7/1980 | Jess et al. | 128/214 E |
| 4,236,880 | 12/1980 | Archibald | 128/214 F X |
| 4,277,227 | 7/1981 | Jenkins | 128/214 E |

*Primary Examiner*—Dalton L. Truluck
*Attorney, Agent, or Firm*—John P. Kirby, Jr.; Eugene M. Cummings; Bradford R. L. Price

[57] ABSTRACT

Metering apparatus for metering the flow of fluid through an administration set includes a peristaltic-type metering pump which repeatedly and progressively compresses a section of vinyl tubing of the administration set to provide a desired flow rate. For improved metering accuracy the fluid is maintained under pressure downline of the metering pump by a downline occlusion station. A protective circuit responsive to the pressure in the tubing downline of the occlusion station stops the metering apparatus and sounds an alarm in the event the pressure in the tubing exceeds a predetermined level, as in the event of an occlusion, downline of the metering apparatus and upline of the patent.

6 Claims, 6 Drawing Figures

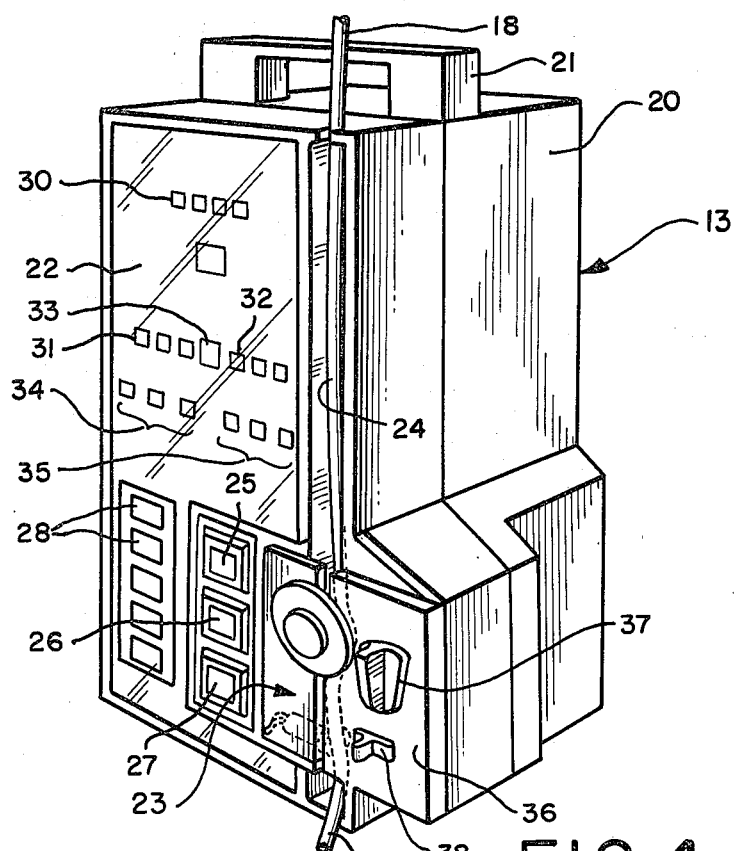
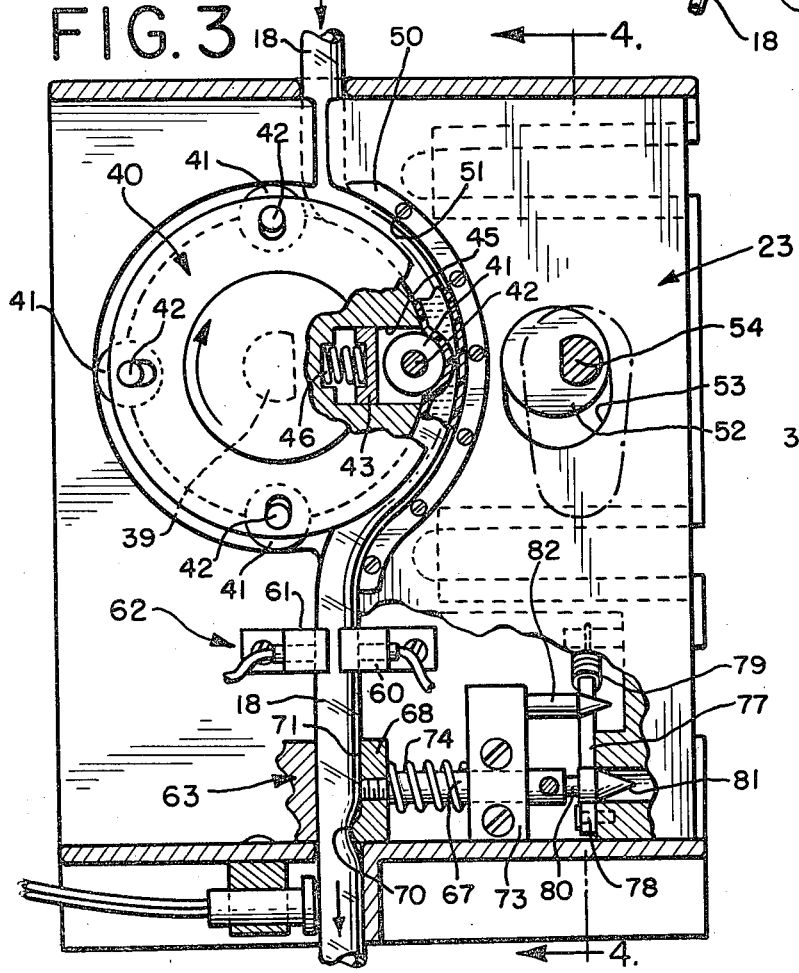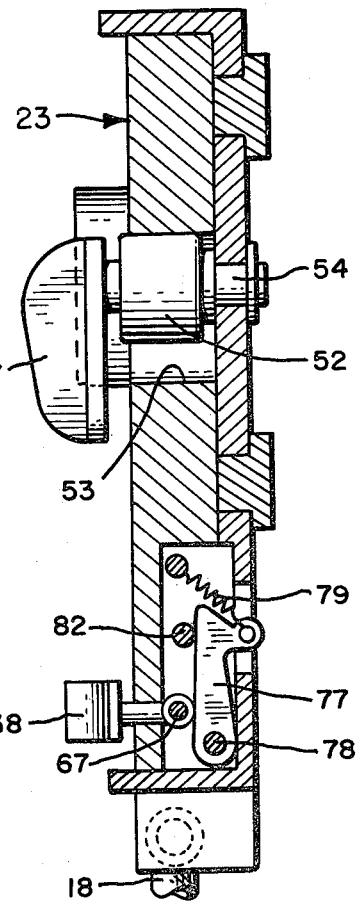

METERING APPARATUS WITH DOWNLINE PRESSURE MONITORING SYSTEM

BACKGROUND OF THE INVENTION

The present invention relates to fluid infusion systems, and more particularly to an improved apparatus for accurately metering the flow rate of fluid through an administration set.

The infusion of fluids such as parenteral solutions and blood into the human body is usually accomplished by means of an administration set in conjunction with metering means for controlling the rate of fluid flow through the set. One form of metering means which is attractive for this application is the peristaltic-type pump, which operates to repeatedly and progressively compress and expand a section of tubing of the administration set so as to cause fluid to flow through the set at a controlled rate, thereby avoiding the need for direct contact with fluid and the attendant risk of contamination.

Because of its partial non-resiliency, tubing formed of vinyl and other thermal plastic materials commonly utilized in administration sets may permanently change its shape and size with time as a result of repeated stretch-compressive cycling, such as it inherent in the operation of a peristaltic-type pump, with the result that the rate at which fluid is delivered by the pump may undesirably vary with time. A system which minimizes the effects of stretch-compressive cycling for improved metering accuracy is described in U.S. Pat. No. 4,155,362, which issued to Thurman S. Jess on May 22, 1979, and is assigned to the present assignee. Basically this system provides for flow restriction means downline of the peristaltic pump to obtain a downline fluid pressure at the point of pump compression which assists in restoring the tubing to its original shape following compression. The flow restriction means perform the additional function of preventing gravity flow in the event the pump head is disengaged by causing a total occlusion of the tubing in the absence of upline pressure. This system has been successfully incorporated in the Model 2M8014 infusion pump manufactured by the Travenol Division of Baxter Travenol Laboratories, Inc., of Deerfield, Illinois.

An additional level of protection against irregular fluid flow is provided by the metering apparatus of the present invention, which monitors fluid pressure in the tubing downline of the occlusion station and interrupts operation of the metering apparatus and sounds an alarm in the event that the pressure rises above a predetermined maximum level, indicating that the tubing has been crimped or occluded between the metering apparatus and the patient.

Prior art systems relied on electrical switches mechanically coupled to a plunger spring-biased against the wall of the tubing and position-dependent on the pressure of the fluid therein for stopping operation of the pump in the event of an occlusion. Unfortunately, the relative insensitivity and inherent unpredictability of switching point of such mechanically-actuated switches to the relatively small pressure changes encountered in the system required setting the threshold level higher than desirable to avoid false alarms during normal operation. As a result, the sensitivity of such systems to occlusions was less than desirable. The present invention is directed to an improved system for detecting downline occlusions which overcomes these limitations on sensitivity.

Accordingly, it is a general object of the present invention to provide a new and improved fluid infusion system.

It is a more specific object of the present invention to provide a new and improved apparatus for infusing fluids into the human body with improved protection against blocked fluid flow.

It is another object of the present invention to provide new and improved metering apparatus for controlling the flow of fluid through the compressible tubing of an administration set wherein operation of the apparatus is interrupted and an alarm is sounded when the fluid pressure downline of the apparatus exceeds a predetermined operating range.

SUMMARY OF THE INVENTION

The invention is directed to a metering apparatus for controlling the flow of fluid through the tubing of an administration set into the human body. The metering apparatus includes a pressure member compressively engaged to the sidewall of the tubing, and drive means for advancing the point of engagement of the pressure member along a segment of the tubing to urge fluid through the tubing downline of the tubing to urge fluid through the tubing downline of the tubing segment, and downline pressure means which continuously at least partially restrict the lumen of the tubing downline of the tubing segment to increase the pressure of the fluid within the segment downline of the point of engagement. A pressure transducer operatively engaged to the tubing downline of the pressurization means develops an output signal continuously indicative of fluid pressure. A pressure monitor circuit responsive to this signal produces an output signal when the downline pressure exceeds a predetermined maximum level to terminate operation of the apparatus and sound an alarm.

BRIEF DESCRIPTION OF THE DRAWINGS

The features of the present invention which are believed to be novel are set forth with particularity in the appended claims. The invention, together with the further objects and advantages thereof, may best be understood by reference to the following description taken in conjunction with the accompanying drawings, in the several figures of which like reference numerals identify like elements, and in which:

FIG. 2 is an enlarged perspective view of the metering apparatus shown in FIG. 1.

FIG. 3 is an enlarged front elevational view of the flow control station of the metering apparatus partially in section and partially broken away to illustrate the principal elements of the station.

FIG. 4 is a cross-sectional view of the flow control station of the metering apparatus taken along line 4—4 of FIG. 3.

DESCRIPTION OF THE PREFERRED EMBODIMENT

Figure 1:
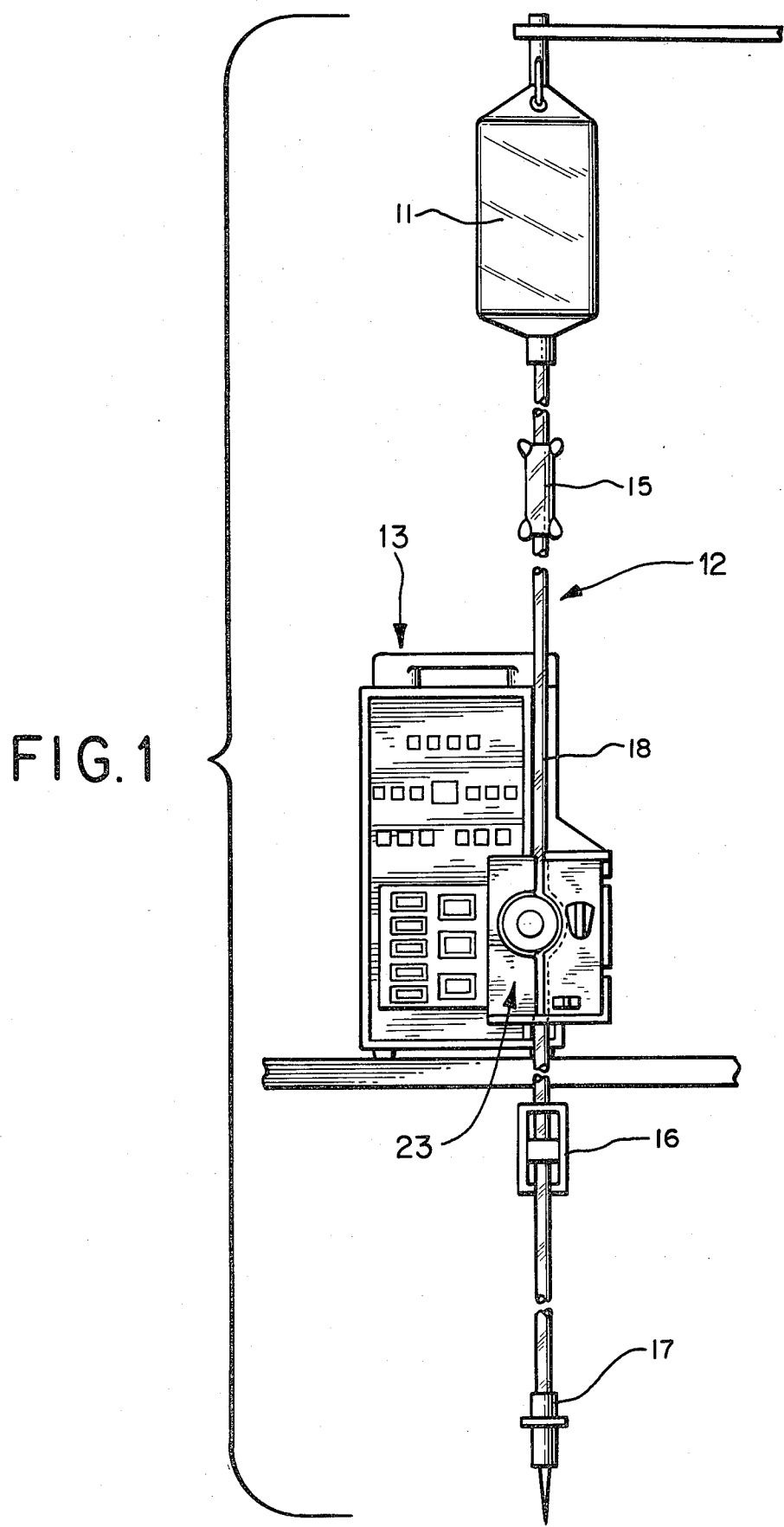
FIG. 1 is a front elevational view of an infusion system incorporating metering apparatus constructed in accordance with the invention.

Referring to the Figures, and particularly to FIG. 1, an infusion system 10 constructed in accordance with the invention for injecting a fluid into a vein or artery of the human body from a reservoir 11 includes a disposable administration set 12 and a flow-controlling metering apparatus 13. The administration set, which may be conventional in design and construction, includes a drip chamber 15, a tubing clamp 16, a needle adapter 17, and a length of flexible transparent tubing 18 preferably formed of a thermo plastic material such as a vinyl. To avoid the danger of contamination, the administration set is packaged in a sterile and non-pyrogenic condition, and is disposed of after a single use.

Referring to FIG. 2, metering apparatus 13, which is utilized in conjunction with administration set 12 for controlling the flow of fluid into a vein or artery, includes a generally rectangular housing 20 having a handle 21 at one end thereof for convenient carrying. The front surface of the housing includes a control panel 22 which allows the operator to control and monitor the operation of the metering apparatus, and a peristaltic-type flow metering station 23 for compressing a section of tubing 18 to effect flow control of fluid in the administration set. A channel 24 is provided above the metering station for maintaining a portion of tubing segment 18 in a convenient position for viewing by the operator whereby flow irregularities can be more readily observed.

The operating mode of the metering apparatus is controlled by means of a push button STOP switch 25, a push button START switch 26, and a push button power ON-OFF switch 27. Each of these push button switches preferably includes an internal indicator lamp which provides a positive indication to the operator of the operating mode of the apparatus. Various abnormal operating conditions are annunciated by means of indicator lights 28 contained on control panel 22 to the left (as viewed in FIG. 2) of the mode control push buttons.

Control panel 22 further includes a digital display 20 of volume infused, a digital display 31 of volume to be infused, and a digital display 32 of fluid flow rate. The volume displayed by display 30 is the volume of fluid actually infused, and can be reset to zero by the operator by means of a push button RESET switch 33. The volume to be infused by display 31 is preset by the operator by means of a set of push button switches 34 to indicate a desired volume of fluid to be infused. Similarly, the infusion rate display 32 is preset by the operator by means of a second set of push button switches 35 to indicate the rate at which infusion is to take place.

The operation of the various indicators, control switches and other features of metering apparatus 13 is described in detail in the copending applications of Thurman S. Jess and Norm Shim, Ser. No. 856,863; Norm Shim, Ser. No. 857,018; Norm Shim and Vincent L. Knigge, Ser. No. 856,927; and Thurman S. Jess, Ser. No. 856,926; all filed Dec. 2, 1977.

The tubing 18 of administration set 12 passes through the flow control station 23 of metering apparatus 13. In accordance with conventional practice the flow control station 23 is provided with a slidably-mounted platen assembly 36 which may be opened by means of a control knob 37 to facilitate insertion or removal of the tubing. Further to this end, an additional control knob 38 is provided to allow user-displacement of a downline occlusion and safety element contained within the flow control station.

Referring to FIG. 3, the flow control station 23 includes metering means in the form of a rotor 40 having four pressure rollers 41 disposed in equi-spaced relationship about its circumference. The rollers are mounted on respective shafts 42 for free rotation, and the shafts are carried on individual carriages 43 mounted on the rotor for reciprocation within respective radial recesses 45. The carriages are spring-biases in a radially outward direction by respective helical springs 46.

The flow control station further includes a pressure plate 50 which provides an arcuate working surface 51 substantially corresponding in shape to the circumference of rotor 40. This surface brings a segment of tubing 18 into compressive engagement with rollers 41 around at least a portion of the rotor circumference corresponding to the distance between adjacent rollers. The pressure plate may be reciprocated toward and away from rotor 40 to facilitate installation and removal of tubing 18 by rotation of an eccentric cam 52, which is constrained to movement within a vertical slot 53 provided on the pressure plate. Rotation of the cam is accomplished by a shaft 54 which connects with knob 37. When knob 37 is in its bottom position, as shown in FIG. 3, the pressure plate is moved sufficiently close to the rotor circumference to cause tubing 18 to be completely occluded by the rollers.

After passing through the peristaltic pump arrangement provided by rotor 40 and pressure plate 50, tubing 18 extends between a light source 60 and a photodetector 61, which together comprise a bubble detector station 62 for detecting the presence of bubbles in the flow system. The tubing then passes through downline pressurization means in the form of a flow restriction station 63. This station includes a slidably-mounted plunger 67 which is biased against the sidewall of tubing segment 18. The end of the plunger which engages the tubing segment includes a generally L-shaped head portion 68 having a wedge-shaped working surface 70 which occludes the tubing and a generally flat control surface 71 on which the fluid acts. The central body portion of the plunger is slidably received within a stationary mounting block 73, and extends through the center of a helical compression spring 74 which biases head 68 into engagement with the tubing.

Plunger 67 may be opened to facilitate loading or unloading of tubing segment 18 by means of the user-actuated knob 38 on the front panel. Automatic release of the plunger is obtained by means of a latch member 77 which is pivotally mounted at 78 to platen assembly 36 and biased by a helical spring 79 for operation within a plane perpendicular to the plunger. The plunger includes a slot 80 in which the latch member 77 is received when the plunger is moved to its full open position. The end 81 of the plunger is tapered to facilitate displacement of the latch member prior to seating in slot 80. Once the latch member has been received in the slot, the plunger is locked open and tubing 18 can be readily removed.

To insure that the plunger will be released when platen assembly 36 is subsequently closed, mounting block 73 is provided with an actuator pin 82 having a tapered end surface which serves to displace the pivotally mounted latch member 77 from slot 80 when the pressure plate is returned to its closed position by rotation of knob 37. In this way, the plunger is automatically released so as to again become spring-biased against the administration set tubing 18 as the metering station is closed. This prevents inadvertent operation of the system without the back pressure and gravity flow protection provided by the plunger.

Figure 5:
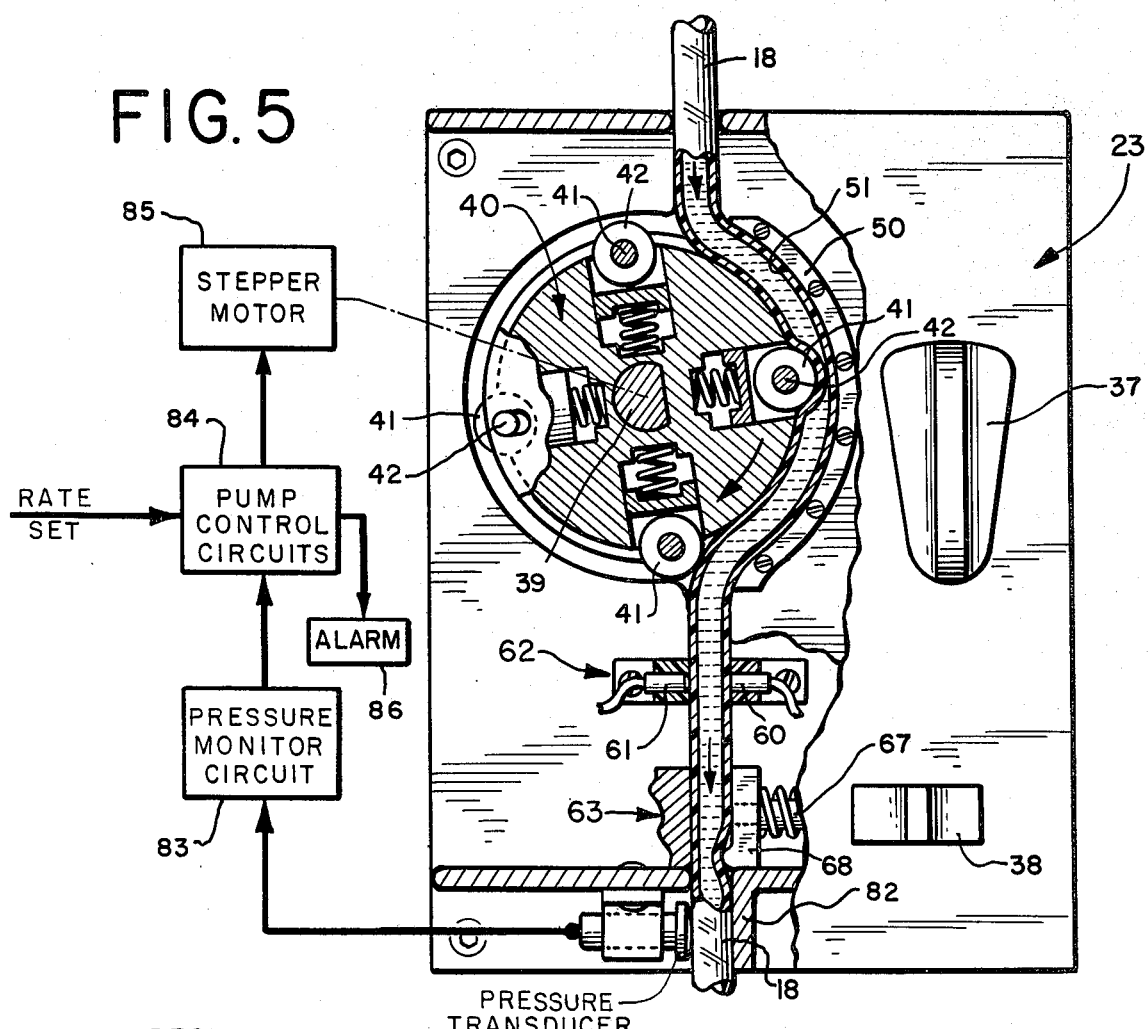
FIG. 5 is a front elevational view of the flow control station partially in section showing the control circuitry of the metering apparatus in functional block design form.

In operation, rotor assembly 40 is rotated clockwise (as viewed in FIG. 3) so as to bring pressure rollers 41 into compressive engagement with tubing 18 against pressure plate 50. As shown in FIG. 5, the force exerted on the tubing by rollers 41 is sufficient to completely occlude the tubing so that as the rotor assembly rotates liquid within the lumen of the tubing is forced to advance. By accurately controlling the speed of rotation of the rotor assembly, it is possible to accurately control the flow rate of fluid through the tubing.

Flow restriction state 63, by partially occluding the tubing, increases the fluid pressure in the lumen of the tubing downline of the point of engagement of the pressure rollers. This pressure assists in expanding the walls of the tubing prior to and following compression by the pressure rollers to their uncompressed shape to minimize variations in the volume of fluid urged forward with each rotation or rotor 40. This feature of the metering apparatus is described in detail in the aforementioned U.S. Pat. No. 4,155,362.

In accordance with the invention, metering apparatus 13 includes a pressure monitoring system 80 for interrupting operation in the event of an occlusion of the tubing downline of the apparatus, or in the event that the tubing breaks or becomes separated from the patient. Referring to FIG. 5, this monitoring system is seen to include a pressure transducer 81 mounted on housing 20 beside and in operative contact engagement with tubing 18 downline of occlusion station 63. A pressure surface 82 is provided on housing 20 opposite the pressure transducer so that changes in pressure within the lumen of the tubing are applied to the sensing surface of the transducer.

The pressure changes at transducer 81 result in the generation of an analog signal having a level indicative of the instantaneous fluid pressure in the tubing. This signal is applied to a pressure monitor circuit 83 wherein it is compared against a predetermined upper limit to determine whether the downline pressure falls within an allowable operating range. In the event that the signal is too high, signifying either a blockage or crimping of the tubing, a control signal is produced.

This control signal is applied to pump control circuits 84, which may be conventional in form and include the necessary power, timing and control circuitry for driving a stepper motor 85 associated with the peristaltic rotor 40 of the metering apparatus. In addition, pump control circuits 84 provide an output signal which is applied to an alarm 86 to cause an audible alarm to be sounded in the event that operation of the metering apparatus is interrupted. The rate at which the rotor turns, and hence the fluid delivery rate of the apparatus, is determined by an input signal applied to the pump control circuits. This rate is normally set by the user by means of appropriate front panel switches and readouts.

Figure 6:
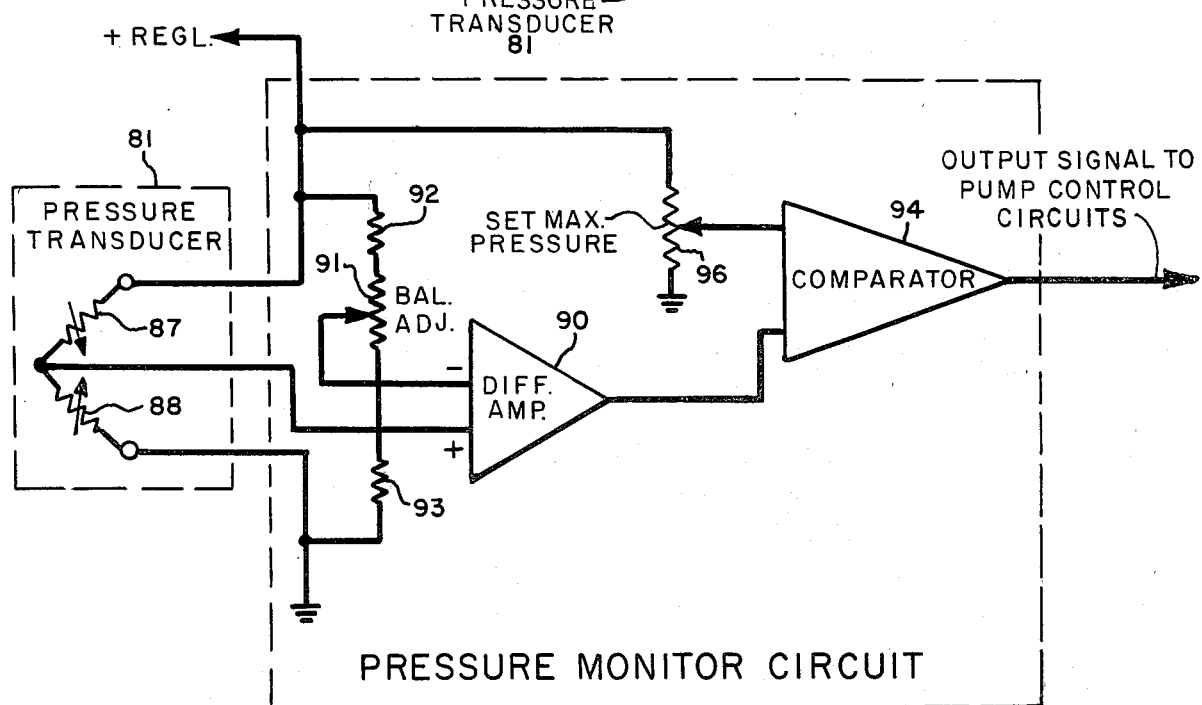
FIG. 6 is a simplified schematic diagram of the pressure monitoring system of the metering apparatus.

Referring to FIG. 6, pressure transducer 81 is seen to comprise, in accordance with conventional practice, a pair of variable resistance elements 87 and 88 which change resistance inversely with changes in applied pressure. One form of pressure transducer commercially available for this application is the type 8805M2 piezoresistive transducer marketed by Endevco, of Capistrano, Calif. The two resistance elements are connected in series between a source of regulated unidirectional current and ground, and the common terminal is connected to the non-inverting terminal of a differential amplifier 90. The inverting terminal of amplifier 90 is connected to the arm of a balance adjust potentiometer 91, which is connected through resistors 92 and 93 to the regulated current source and ground.

The output of differential amplifier 90 is connected to one input of a comparator 94. The remaining input of comparator 94 is connected to an upper limit voltage source comprising a first potentiometer 96. Potentiometer 96 is connected between the regulated current source and ground.

In operation, the voltage level at the noninverting input of differential amplifier 90 is a function of the downline pressure as applied by the sidewall of tubing 18 to transducer 81. By adjusting potentiometer 91 the voltage level at the inverting input of amplifier 90 is set so that the output of the differential amplifier as applied to voltage comparators 94 and 95 is at a predetermined reference level when the downline pressure is at a nominal level. As the pressure increases, the output of differential amplifier 90 rises above the reference level, until it reaches the maximum pressure reference level applied to the other input of comparator 94, causing that device to produce an output signal. This output signal, when applied to pump control circuits 84 stops operation of the pump and causes alarm 86 to be sounded. Thus, operation is terminated and an alarm is sounded in the event of either a high pressure condition or a low pressure condition.

In practice, potentiometer 96 may be set so that when fluid pressure increases above the 5-10 psi pressure range encountered during normal operation and reaches approximately 12-15 psi, an output signal is produced by comparator 94 and operation of the pump is stopped. The 12-15 psi pressure threshold is considerably lower than the 30-40 psi minimum threshold levels possible with mechanically-actuated switches, thereby providing greater occlusion detection sensitivity.

By deriving an analog signal representative of downline pressure level over a wide operating range, the pressure monitoring circuit of the invention avoids the need for the precision switches, mechanical linkages and precise adjustments which would be required with the use of pressure-actuated switches. It will be appreciated that other types of pressure sensors can be used, such as a Hall Effect device of the type which provides an analog output in response to applied pressure. In this device a magnet is mounted for pressure-responsive movement, and a magnetically sensitive Hall Effect analog sensor responds to the field of the magnet to provide an analog output signal. One such device is commercially available as the Model UGN-3600M sensor manufactured by Sprague Electric Company of Concord, N.H. Other types of devices useful for this application include linear voltage differential transformers (LVDT's) and rotary voltage differential transformers (RVDT's).

While a particular embodiment of the invention has been shown and described, it will be obvious to those skilled in the art that changes and modifications may be made without departing from the invention in its broader aspects, and, therefore, the aim in the appended claims is to cover all such changes and modifications as fall within the true spirit and scope of the invention.

I claim:

1. A flow system for infusing a fluid from a supply reservoir into the human body, comprising, in combination:
   a length of flexible-walled tubing extending from the supply reservoir to the body;
   metering means continuously including at least one pressure member compressively engaged to the sidewall of said tubing for occluding the lumen thereof;
   drive means for advancing the point of engagement of said pressure member along a segment of said tubing to urge fluid through said tubing;
   downline pressurization means comprising a plunger spring-biased against said tubing downline of said tubing segment for continuously at least partially restricting the lumen of said tubing to increase the pressure of the fluid within said segment downline of said point of engagement;
   pressure sensing means including a pressure transducer operatively engaging said tubing downline of said pressurization means for producing an output signal having a level continuously indicative of the downline pressure level in the tubing; and
   pressure monitor circuit means responsive to said output signal for terminating operation of said drive means in the event said pressure level reaches a predetermined maximum level.

2. A flow system as defined in claim 1 wherein said pressure sensing means comprise a pressure transducer providing a continuous analog output signal.

3. A flow system as defined in claim 2 wherein said pressure monitor circuit means include a comparison amplifier providing a control signal upon said analog output signal reaching a predetermined reference level corresponding to said predetermined maximum pressure level.

4. Metering apparatus for infusing a fluid from a supply reservoir to the human body through a length of flexible-walled tubing, comprising, in combination:
   metering means continuously including at least one pressure member compressively engaged to the sidewall of the tubing for occluding the lumen thereof;
   drive means for advancing the point of engagement of said pressure member along a segment of the tubing to urge fluid through the tubing;
   downline pressurization means comprising a plunger spring-biased against the tubing downline of said tubing segment for continuously at least partially restricting the lumen of the tubing to increase the pressure of the fluid within said segment downline of said point of engagement;
   pressure sensing means including a pressure transducer operatively engaging the tubing downline of said pressurization means for producing an output signal having a level continuously indicative of the downline pressure level in the tubing; and
   pressure monitor circuit means responsive to said output signal for terminating operation of said drive means in the event said pressure level reaches a predetermined maximum level.

5. Metering apparatus as defined in claim 4 wherein said pressure sensing means comprise a pressure transducer providing a continuous analog output signal.

6. Metering apparatus as defined in claim 5 wherein said pressure monitor circuit means include a comparison amplifier providing a control signal upon said analog output signal reaching a predetermined reference level corresponding to said predetermined maximum pressure level.

* * * * *